(12) United States Patent
Yatscoff et al.

(10) Patent No.: US 6,602,715 B2
(45) Date of Patent: *Aug. 5, 2003

(54) ¹³C GLUCOSE BREATH TEST FOR THE DIAGNOSIS OF DIABETIC INDICATIONS AND MONITORING GLYCEMIC CONTROL

(75) Inventors: Randall W. Yatscoff, Edmonton (CA); Robert T. Foster, Edmonton (CA); Launa J. Aspeslet, Edmonton (CA); Richard Lewanczuk, Edmonton (CA)

(73) Assignee: Isotechnika Inc., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/228,276

(22) Filed: Aug. 27, 2002

(65) Prior Publication Data

US 2003/0044993 A1 Mar. 6, 2003

Related U.S. Application Data

(63) Continuation of application No. 09/674,806, filed as application No. PCT/IB99/00933 on May 6, 1999, now Pat. No. 6,468,802.
(60) Provisional application No. 60/084,482, filed on May 6, 1998.

(51) Int. Cl.⁷ .............................................. G01N 37/00
(52) U.S. Cl. ......................... 436/56; 436/14; 436/173; 436/181; 422/61; 435/14
(58) Field of Search ........................ 436/56, 173, 181, 436/814, 8, 14; 422/61; 435/14

(56) References Cited

U.S. PATENT DOCUMENTS

| | | | |
|---|---|---|---|
| 5,912,178 A | 6/1999 | Porter et al. | |
| 5,916,538 A | 6/1999 | Kohno et al. | |
| 5,962,335 A | 10/1999 | Katzman | |
| 6,067,989 A | 5/2000 | Katzman | |
| 6,171,811 B1 | 1/2001 | Becerro de Bengou Vallejo | |
| 6,461,870 B2 * | 10/2002 | Yatscoff et al. | 436/56 |
| 6,468,802 B1 * | 10/2002 | Yatscoff et al. | 436/56 |

FOREIGN PATENT DOCUMENTS

| | | |
|---|---|---|
| EP | 0826377 A1 | 3/1998 |
| EP | 0913161 A2 | 5/1999 |

OTHER PUBLICATIONS

Beck et al., *Metabolic and Genetic Characterization of Pre–diabetic States. Sequence of Events Leading to Non–insulin–dependent Diabetes Mellitus.* J Clin Invest, 94, (1994), pp. 1714–1721.

Bonora et al., *Homeostasis Model Assessment Closely Mirrors the Glucose Clamp Technique in the Assessment of Insulin Sensitivity*, Diabetes Care, 23, (2000), pp. 57–63.

CDC Diabetes Cost–Effectiveness Study Group, *The Cost–Effectiveness of Screening for Type 2 Diabetes*, JAMA, 280, (1998), pp. 1757–1763.

Emoto et al., *Homeostasis Model Assessment as a Clinical Index of Insulin Resistance in Type 2 Diabetic Patients Treated With Sulfonylureas*, Diabetes Care, 22, (1999), pp. 818–822.

The Expert Committee on the Diagnosis and Classification of DiabetesMellitus, *Report of the Expert Committee on the Diagnosis and Classification of Diabetes Mellitus*, Diabetes Care, 24, (2001), suppl 1.

Gabir et al., *The 1997 American Diabetes Association and 1999 World Health Organization Criteria for Hyperglycemia in the Diagnosis and Prediction of Diabetes*, Diabetes Care, 23, (2000), pp. 1108–1112.

Ganda et al., *Reproducibility and Comparative Analysis of Repeated Intravenous and Oral Glucose Tolerance Tests*, Diabetes, 27, (1978), pp. 715–725.

Haffner et al., *A Prospective Analysis of the HOMA Model: The Mexico City Diabetes Study*, Diabetes Care, 19, (1996), pp. 1138–1141.

Harris, M.I., *Undiagnosed NIDDM: Clinical and Public Health Issues*, Diabetes Care, 16, (1993), pp. 642–652.

Helge et al., *Carbon–13 Dioxide Breath Tests in Normal and Diabetic Children Following Ingestion of ¹³C–Glucose*, Chemical Abstract Service, Database accession No. 90:37276, XP002120262. (Abstract).

Hirai et al., *The Breath Test Using Pure (1–¹³C) Glucose: A New Simple Method for Evaluating the Glucose Oxidation of Capacity*, Biosciences Information Services, retrieved from STN, XP002120264. (Abstract).

Hosker et al., *Continuous Infusion of Glucose with Model Assessment: Measurement of Insulin Resistance and β–cell Function in Man*, Diabetologia, 28, (1985), pp. 401–411.

Ko et al., *Use of the 1997 American Diabetes Association Diagnostic Criteria for Diabetes in a Hong Kong Chinese Population*, Diabetes Care, 21, (1998), pp. 2094–2097.

Ko et al., *The Reproducibility and Usefulness of the Oral Glucose Tolerance Test in Screening for Diabetes and Other Cardiovascular Risk Factors*, Ann. Clin. Biochem., 35, (1998), pp. 62–67.

Lifschitz et al., Journal of Pediatric Gastroenterology and Nutrition, vol. 7(6), pp 842–847 (Nov.–Dec. 1988). (Abstract).

Lillioja et al., *Insulin Resistance and Insulin Secretory Dysfunction as Precursors of Non–insulin–dependent Diabetes Mellitus; Prospective Studies of Pima Indians*, New England Journal of Medicine, 329, (1993), pp. 1988–1992.

(List continued on next page.)

Primary Examiner—Maureen M. Wallenhorst
(74) Attorney, Agent, or Firm—Burns Doane Swecker & Mathis LLP

(57) ABSTRACT

A breath test and kit for performing the breath test are described for the diagnosis of diabetic indications and monitoring of glycemic control. The breath test utilizes the measurement of expired ¹³C-labeled $CO_2$ following the ingestion of a ¹³C-enriched glucose source.

42 Claims, 5 Drawing Sheets

OTHER PUBLICATIONS

Martin et al., *Role of Glucose and Insulin Resistance in Development of Type 2 Diabetes Mellitus: Results of a 25-year Follow-up Study,* Lancet, 340, (1992), pp. 925–929.

Matthaei et al., *Pathophysiology and Pharmacological Treatment of Insulin Resistance,* Endocr. Rev., 21, (2000), pp. 585–618.

Matthews et al., *Homeostasis Model Assessment: Insulin Resistance and Beta-cell Function from Fasting Plasma Glucose and Insulin Concentrations in Man,* Diabetologia, 28, (1985), pp. 412–419.

McAuley et al., *Diagnosing Insulin Resistance in the General Population,* Diabetes Care, vol. 24, No. 3, (Mar. 2001), pp. 460–464.

Meltzer et al., 1998 *Clinical Practice Guidelines for the Management of Diabetes in Canada.,* Canadian Medical Association Journal, 159, (1998), (suppl. 8): S1–29.

Radziuk, J., *Insulin Sensitivity and Its Measurement: Structural Commonalities Among the Methods,* Journal of Clinical Endocrinol Metab., 85, (2000), pp. 4426–4433.

Riccardi et al., *Reproducibility of the New Diagnostic Criteria for Impaired Glucose Tolerance,* Am. J Epidemiol, 121, (1985), pp. 422–429.

Rocker et al., *Breath–by–Breath Measurements for the Analysis of Exogenous Glucose Oxidation During Intense Endurance Exercise* (Using [$^{13}$C]–Isotopes, Int. Journal of Sports Medicine, vol. 17, pp 480–486 (1996).

Tanis et al., *Human Liver Glycogen Metabolism Assessed with a $^{13}$C–enriched Diet and a $^{13}CO_2$ Breath Test,* Biosciences Information Services, retrieved from STN, XP002120263. (Abstract).

World Health Organization, *Prevention of Diabetes Mellitius: Report of a WHO Study Group,* Geneva: WHO, (1994), Technical Report Series No. 844.

World Health Organization, *Definition, Diagnosis and Classification of Diabetes Mellitus and its Complications,* Report of a WHO Consultation, Part 1, Diagnosis and Classification of Diabetes Mellitus, Geneva: WHO, (1999).

\* cited by examiner

FIG_3

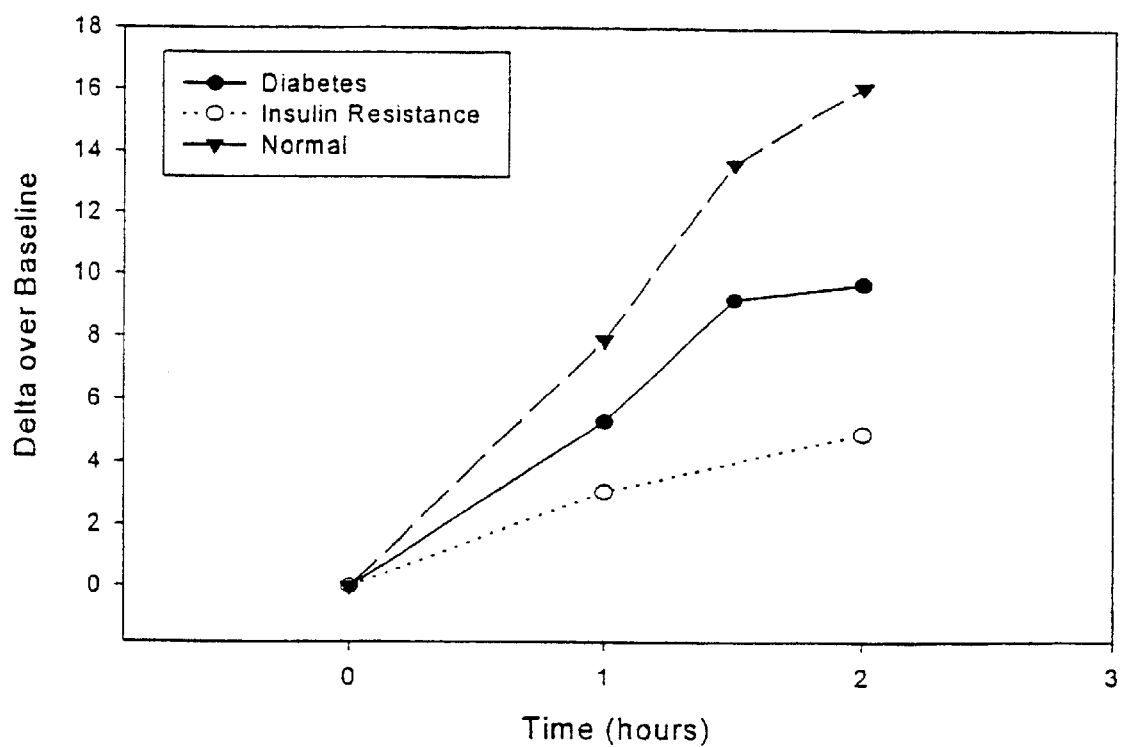

$^{13}$C GLUCOSE BREATH TEST FOR THE DIAGNOSIS OF DIABETIC INDICATIONS AND MONITORING GLYCEMIC CONTROL

REFERENCE TO RELATED APPLICATION

This application is a continuation of U.S. application Ser. No. 09/674,806, filed Feb. 8, 2001, now U.S. Pat. No. 6,468,802, which is a U.S. National Phase Application of International Application PCT/IB99/00933, filed May 6, 1999, which claims priority to U.S. Provisional Application No. 60/084,482, filed May 6, 1998. The disclosure of each of the above applications is incorporated herein by reference in their entirety.

BACKGROUND OF THE INVENTION

Glucose tolerance is defined as the ability to properly utilize glucose. Diabetes is not a single disease, but an array of diseases that exhibit the common symptom of glucose intolerance, an impairment in glucose utilization.

The prevalence of diabetes in the general population is approximately 6–7%. Only about half of diabetics are actually diagnosed. Studies have shown that rates for persons with glucose intolerance are equal by sex and greater for blacks than for whites.

In general, the following types of diabetes have been recognized: type I diabetes mellitus, type II diabetes mellitus, secondary diabetes mellitus, impaired glucose tolerance and gestational diabetes mellitus. The general characteristics of the symptoms of diabetes include the following:

- Polyuria (excretion of large quantities of urine)
- Hyperglycemia (high blood glucose levels)
- Glucosuria ( abnormal presence of glucose in urine)
- Polydipsia (excessive thirst)
- Polyphagia (excessive hunger)
- Sudden weight loss.

It has been observed that complications resulting from diabetes mellitus are the third leading cause of death in most developed countries. Diabetes is a risk factor for a variety of conditions including coronary heart disease, cerebrovascular stroke, neuropathy (nerve damage), nephropathy (kidney damage), retinopathy (eye damage), hyperlipidemia (excessive blood lipids), angiopathy (damage to blood vessels) and infection.

A number of different methods exist for determining a condition of intolerance for glucose. These include post-prandial blood glucose, oral glucose tolerance test (OGTT), O'Sullivan glucose tolerance test (gestational test), hemoglobin Alc (Hb $A_1$, Hb $A_{1c}$), islet cell antibodies, GAD antibodies (glutamic acid decarboxylase) and insulin antibodies. Diabetes, however, is most readily detected when the carbohydrate metabolic capacity is tested. This is done by stressing the system with a defined glucose load as in the oral glucose tolerance test (OGTT).

The OGTT has been criticized, however, because many of the variables affecting test results are difficult to control, for instance: Patients must be on a standardized carbohydrate diet at least three days before the test. The test requires an 8 to 16 hour fast. The test should only be performed on ambulatory patients. Stress should be avoided. Exercise should be avoided. Various hormone imbalances can affect validity such as with: thyroxine, growth hormone, cortisol and catecholamines. Various drugs and medications can affect validity such as: oral contraceptives, salicylates, nicotinic acid, diuretics and hypoglycemics. Evaluation should normally be corrected for age. The greatest disadvantage of the OGTT is that it is poorly reproducible and this limits its diagnostic usefulness.

The current methods of diagnosing diabetes involve either invasive testing (ie. repeated blood collections), or use blood-borne markers (ie. glycosylated proteins, or antibodies) which offer an indirect assessment of glucose regulation. Accordingly, it is an object of the present invention to avoid the need for invasive testing or the use of blood-borne markers in determinations of glucose regulation.

SUMMARY OF THE INVENTION

The above and other objects of the invention are attained by a $^{13}$C breath test and a kit for determining glucose regulation in a patient in need thereof.

An analytical assay is described that is based on the use of non-radioactive $^{13}$C. Labeled expired $^{13}CO_2$ is measured in the present assay. Isotope ratio mass spectroscopy (IRMS) is used as a detection method for $^{13}$C, a non-radioactive isotope that occurs naturally in food and animal tissues. Non-dispersive infrared spectroscopy (NDIRS) analysis and analysis methods known in the art may be employed. The test protocol is as follows: after an overnight fast, the oral dose of $^{13}$C uniformly labeled glucose (containing about 25 mg of $^{13}$C glucose in combination with about 15 g of unlabeled glucose in 100 mL of tap water) is administered. Breath samples will be collected before the dose and then 1½ hours after $^{13}$C glucose ingestion. Levels of $^{13}CO_2$ in expired air will be measured by an IRMS method.

Advantages of this test are the following:

- it is practical, sensitive and specific;
- the validity of the test is not influenced by stress, exercise, hormone imbalances, or some drugs and medications
- it is a non-invasive method;
- it is simple to perform and can be readily used in physicians' offices or medical laboratories;
- it is safe since $^{13}$C is a naturally occurring isotope found in all carbon-containing substances;
- it involves no radioactivity, and may be used in children and women.

The $^{13}$C glucose test is safe, reliable, and specific in diagnosis of diabetes and measurement of the severity of insulin resistance in patients. The invention is also preferred to diagnose gestational diabetes and to monitor glycemic control in diabetes patients. A preferred embodiment of the invention is a kit containing the necessary material for performing the described method. This kit may contain but is not limited to a source of $^{13}$C enriched glucose (preferably uniformly labeled D-glucose); a source of unenriched glucose; and a breath collection device. The kit may also contain a set of patient instructions for its use. In another embodiment, the kit may additionally contain a blood collection device such as a lancet or hypodermic needle and vacutainer for the additional determination of blood glucose levels.

BRIEF DESCRIPTION OF THE DRAWINGS

FIG. 5: Shows a comparison of IRMS results of an insulin resistant and a diabetic patient and a normal individual.

DETAILED DESCRIPTION OF THE INVENTION

Figure 1:
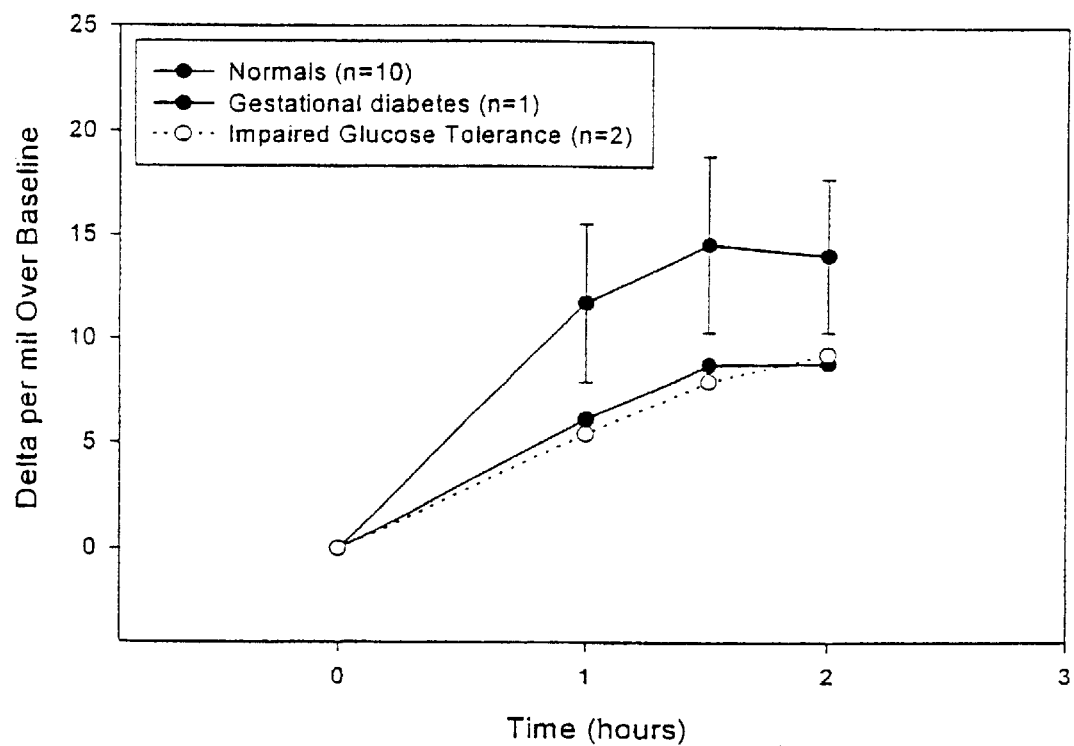
FIG. 1: Illustrates the IRMS analysis of $^{13}$C glucose breath samples from normal individuals, a gestational diabetic and patients with impaired glucose tolerance.

The introduction of a $^{13}C$ breath test offers a novel, non-invasive, direct means to monitor glucose metabolism by measurement of exhaled $CO_2$ using highly enriched, uniformly labeled $^{13}C$-glucose. Glucose metabolism will generate labeled $CO_2$, which is then exhaled and collected in tubes. Enrichment of labeled $CO_2$, over a determined time course, can be used as a quantitative index of glucose metabolism. Comparison is made against age-specific reference intervals.

The present invention has a number of advantages, including lower dose of glucose needed (overcomes inconsistencies due to malabsorptive disorders or previous gastric or intestinal surgery), reduction in testing time (from the current 2 hours required for the OGTT) and fewer interpretational ambiguities (greater sensitivity and specificity).

The $^{13}C$ glucose breath test is based on the metabolism of glucose. Following a baseline breath sample, a $^{13}C$ glucose solution containing about 25 mg of $^{13}C$ glucose in combination with about 15 g of unlabeled glucose in 100 mL of tap water is administered. Breath samples will be obtained before the dose and then 12 hours after $^{13}C$ glucose ingestion. Measurement of the expired air will be detected by an isotope ratio mass spectroscopy assay method. Elevated or excessive breath 13CO2 concentrations will be seen in individuals who have normal glucose metabolism.

The following Examples serve to illustrate the present invention. These Examples are not intended to limit the scope of the invention in any manner.

EXAMPLE 1

Sample Assay for Diagnosis of a Patient

Experimental Procedure

Medical History

Medical history is taken and includes, but is not limited to: the absence of active pulmonary disease, no history of heart, liver, or renal failure, and no use of insulin or oral medications for the treatment of diabetes.

Physical Examination and Laboratory Tests

No physical examination or laboratory tests, including blood sampling, is required.

Dietary Control

It is determined that all participants have fasted overnight prior to commencement of the test.

Patient Control

Participants are not permitted to eat, drink, or smoke during the test. All patients are required to remain sedentary for the duration of the test. Small amounts of water are allowed.

Assay Procedure

Patients fast for at least 8 hours before this test.

A sample set of patient instructions is given below:

Step 1: COLLECT FIRST BREATH SAMPLE

Remove the screw cap from the collection tube.

Take a normal breath and then exhale fully 4 to 8 seconds through a straw into the bottom of the collection tube.

Immediately replace the screw cap on the collection tube and tighten until snug (do not overtighten).

Affix the completed green label to the collection tube.

Step 2: DRINK THE SOLUTION

Prepare the solution by adding tap water to the fill line on the plastic container. Mix until completely dissolved and then drink the entire solution.

Wait 1½ hours.

Step 3: COLLECT THE SECOND BREATH SAMPLE

One and one half hours after drinking the solution, collect the second breath sample into the collection tube following the same directions as for the first breath sample in step 1.

Affix the completed yellow label to the tube.

Step 4: RETURN THE SAMPLES FOR ANALYSIS

Insert the 2 collection tubes along with the signed and completed registration card in the mailing box.

Return the mailing box as instructed to the site of dispensing.

EXAMPLE 2

Breath Test Administration

Patients are given an exetainer tube with the screw cap removed. Using the straw, they are asked to breathe into the tube, exhaling normally, for 4 to 8 seconds. Next, each patient is instructed to drink a solution containing about 25 mg of uniformly labeled $^{13}C$ glucose in combination with about 15 g of unlabeled glucose in 100 mL of tap water. After 12 hours, the patients are given a new tube to breathe in as described above. The breath collection is then complete.

Storage and Shipping

Breath test tubes are typically labeled with the patient's name and identification number and shipped to an analytical laboratory for analysis. No refrigeration or special storage techniques are necessary.

EXAMPLE 3

Analytical Methodology

Breath specimens are analyzed by isotope ratio mass spectroscopy. NDIRS is also a preferred method to analyze breath test samples. Other methods known in the art may also be used.

Statistical Analysis

The sensitivity, specificity, positive and negative predictive values of the breath test are compared to that of the oral glucose tolerance test. Receiver operator characteristic curve analysis is performed to confirm the discrimination between type 2 diabetes or gestational diabetes and individuals with normal glucose metabolism.

EXAMPLE 4

Basis of the Method of IRMS

Isotope ratio mass spectroscopy (IRMS) is a highly precise method of analysis which is able to measure small samples (low nanogram amounts). For example, $^{13}C/^{12}C$ ratios are determined on a mono-carbon molecule; $CO_2$ gas. The $CO_2$ gas can be directed to the spectrometer by means of a continuous flow IRMS (also called CF-IRMS).

The statistical combination of the isotopes of carbon ($^{12}C$ and $^{13}C$) and oxygen ($^{16}O$, $^{17}O$, $^{18}O$) to generate the $CO_2$ molecules gives rise to the formation of various isotopomers whose molecular weights are 44, 45, and 46, respectively. Thus, for measuring carbon isotope ratios, three ion beams are generated and recorded in the IRMS, corresponding to the masses of the various isotopomers of $CO_2$.

In order to obtain a high precision and a high accuracy, reference gases of absolutely known isotopic composition are used and a dual inlet system allows an alternative admission of both sample and reference gases into the ionization source via a gas-switching valve. The measurement of the various ion beams allows for the calculation of the $^{13}C$ enrichment of the sample. The value of this calculation is given $\delta^{13}C(\%)$ notation. The $^{13}C$ abundance is expressed as $\delta^{13}C(\%)$ according to the following:

$$\delta^{13}C(\%)=([(^{13}C/^{12}C) \text{ sample}/(^{13}C/^{12}C)PDB]-1)\times 1000$$

This $\delta^{13}C(\%)$ value measures the variations in parts per thousand of the carbon isotope ratio from the standard. For carbon, PDB was selected as the international reference. PDB is Pee Dee Belemnitella (a fossil from the Pee Dee geological formation in South Carolina). The $^{13}C/^{12}C$ ratio from the calcium carbonate of this fossil is 0.011237. Compared to PDB, most of the natural compounds display a negative delta value. In the above equation, $^{13}C/^{12}C$ refers to the isotopomers.

Using the breath test of this invention, IRMS is an example method to diagnose type 2 and gestational diabetes, and for monitoring glycemic control of diabetes patients.

EXAMPLE 5

$^{13}C$ Glucose Breath Test Results of Normal, Gestational Diabetes and Impaired Glucose Tolerance Patient Example 4 describes a method to analyze breath samples of this invention. FIG. 1 shows the mean (±SD) Delta per mil over Baseline (DOB) of the normal population. Also shown are the DOB's of a gestational diabetic and impaired glucose tolerance patients. Breath samples collected 0, 1, 1.5 and 2 hours according to the protocol were analyzed by IRMS. IRMS analysis of the collected breath samples can be performed on various instruments, including but not limited to the AP2003 and AP2002 (Analytical Precision Ltd), ABCA (POZ Europa) and the Breath MAT (Finnigan MAT). The DOB values of the gestational diabetes and the impaired glucose tolerance patients are well below the DOB of the normal population (FIG. 1). The impaired glucose tolerance diagnosis was initially determined by OGTT, the gestational diabetes screen was used to confirm gestational diabetes.

Impaired glucose tolerance (IGT) refers to a condition in which blood sugar levels are higher than normal, but are not high enough to be classified as diabetes. IGT is a major risk factor for type 2 diabetes. IGT is present in about 11 percent of adults, or approximately 20 million Americans. About 40–45 percent of persons age 65 years of age or older have either type 2 diabetes or IGT. A person is currently diagnosed with IGT when the 2-hour glucose results from a glucose tolerance test are greater than 7.8 mmol/L, but less than 11.0 mmol/L. A woman is diagnosed with gestational diabetes when she is pregnant and has any two of the following: a fasting plasma glucose of more than 5.3 mmol/L, a 1-hour glucose level of more than 10.6 mmol/L, a 2-hour glucose level of more than 8.9 mmol/L. However, as this method of diagnosis is invasive, the breath tests of the current invention is the preferred diagnosis method. The $^{13}C$ glucose breath test is sensitive, accurate and non-invasive.

EXAMPLE 6

Figure 2:
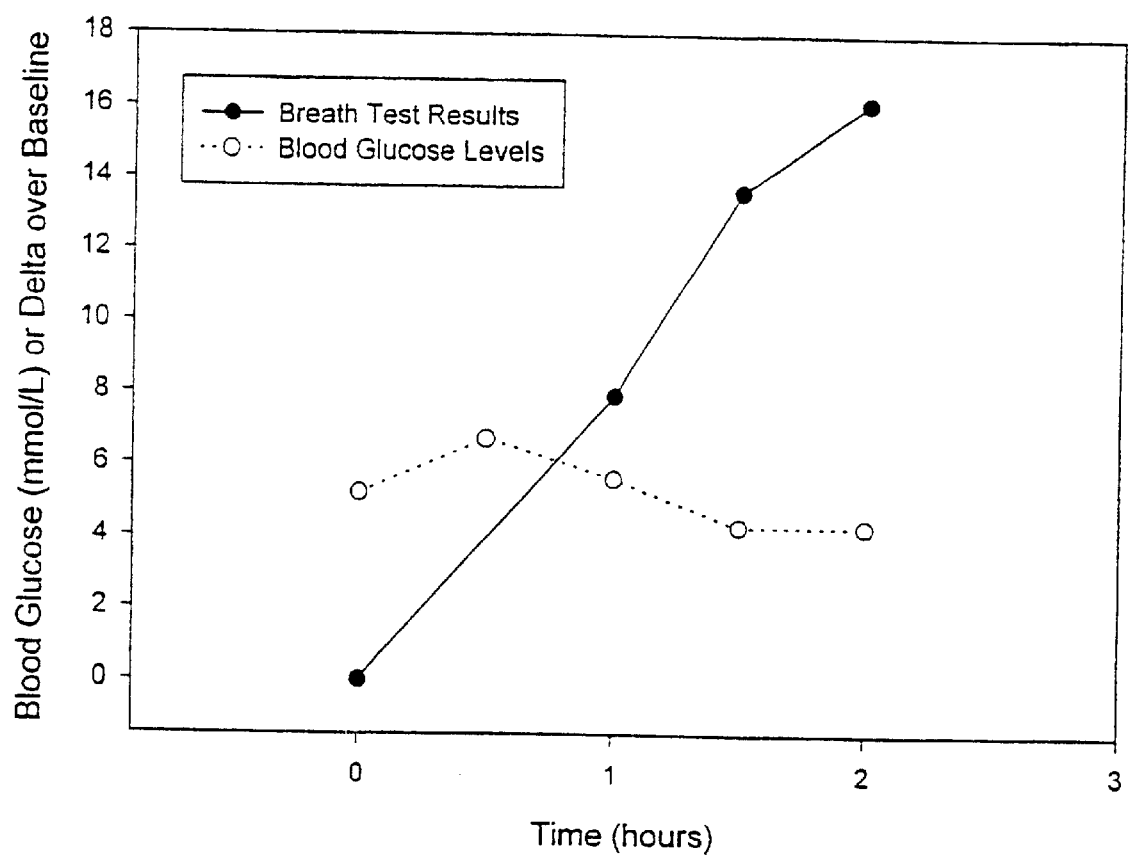
FIG. 2: Shows a representative example of breath test and blood glucose levels of a normal individual.

$^{13}C$ Glucose Breath Test Results of a Normal, Insulin Resistant and Diabetes Patient In this example, both breath test and blood glucose levels were done on a normal, diabetic and insulin resistant patient. FIG. 2 shows the DOB of 0, 1, 1.5 and 2 hours breath samples of a normal subject analyzed by IRMS. The blood glucose level of this normal individual is also displayed.

Figure 3:
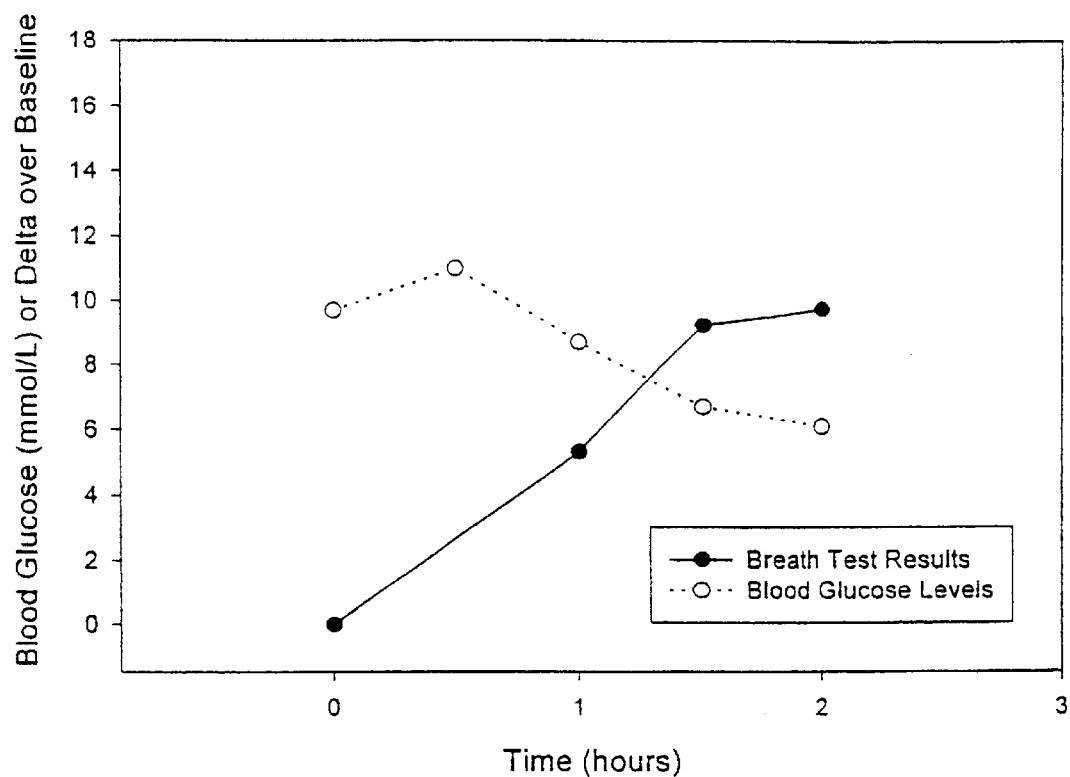
FIG. 3: Illustrates breath test and blood glucose levels of a diabetic patient.

FIG. 3 illustrates the breath test and blood glucose levels of a diabetic patient. The DOB of the breath samples are significantly lower than the DOB of the normal individual (FIG. 2), the blood glucose levels are typical of a diabetic patient.

Figure 4:
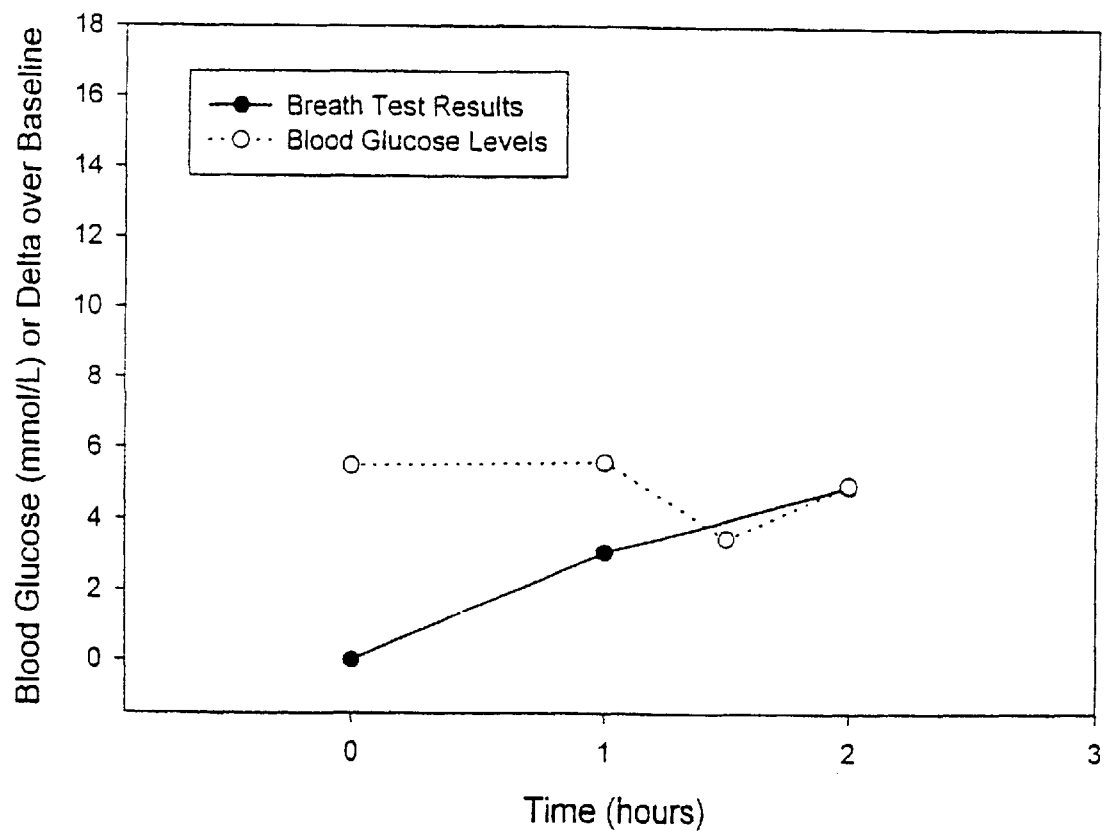
FIG. 4: Depicts breath test and blood glucose levels of an insulin resistant patient.

In FIG. 4, the breath test and blood glucose levels of an insulin-resistant patient are depicted. The DOB of these breath samples are significantly lower than the normal DOB (FIG. 2), the blood glucose levels are typical of an insulin-resistant patient.

These results demonstrate one preferred utility of the breath test of the current invention to diagnose diabetes and insulin resistance. In another aspect of the invention, the areas between the breath test and blood glucose test curves can be used to diagnose patients with insulin resistant or diabetes and confirm glucose tolerance in normal individuals by the comparison of the areas to the different groups of normal, diabetic and insulin resistant patients.

FIG. 5 illustrates the $^{13}C$ glucose breath test results of a normal individual, insulin resistant and diabetes patient. The DOB's of the insulin resistant and diabetes patients is significantly lower than that of the normal DOB results.

EXAMPLE 7

NDIRS Instrumentation

Breath test samples of the invention can also be analyzed using NDIRS instrumentation. The course of the $^{13}CO_2/^{12}CO_2$ ratio in breath allows for diagnosis of diabetes. NDIRS can be further used to diagnose type 2 and gestational diabetes patients and for monitoring therapy of diabetes patients (glycemic control of these patients).

The metabolism of $^{13}C$ labeled substrate leads to a different isotope ratio. NDIRS analysis of the invention can be performed on various instruments, including but not limited to the MicroLyzer (QuinTron), UbiT-IR200 and UbiT-100 (Otsuka Pharmaceutical Co., Ltd.), the URAS 10 (Hartmann and Braun) and the Isomax 2000 (Isotechnika).

EXAMPLE 8

Hyperinsulinemic Euglycemic Clamp Method for the Measurement of Insulin Resistance Insulin resistance is defined as the decrease of the biological action of insulin, and it mainly presents as an hyperinsulinemia. The hyperinsulinemic euglycemic clamp is currently the reference method for quantifying insulin resistance. The clamp technique consists of infusing insulin at a constant rate and, to prevent any decrease in the plasma glucose level, by infusing dextrose. The rate of dextrose infused to maintain euglycemia is an estimate of the amount of glucose, which is taken up by the tissues under the effect of a defined plasma insulin concentration. Using several rates of insulin infusion allows the establishment of the relationship between the whole body glucose disposal and plasma insulin levels, and to discriminate between the states of decreased insulin sensitivity and/or altered maximal capacity to dispose of glucose. However, the hyperinsulinemic euglycemic clamp method is very invasive, time consuming, costly and variable. The breath test of this invention is a preferred method to measure insulin resistance as it is reliable, sensitive, specific, cost-effective and non-invasive.

EXAMPLE 9

Monitoring Long-Term Control of Diabetes

Measuring glycated hemoglobin is a current test used for monitoring long-term control of diabetes. Glycated hemoglobins are increased as a reflection of hyperglycemia during the lifespan of erythrocytes. However, different analytical methods may measure different glycated hemoglobins and caution must be exercised in the interpretation of results. HPLC or column chromatography methods used to analyse glycated hemoglobin are also highly sensitive to variations in temperature and pH. This test is also invasive, requiring several blood samples. The breath test of the present invention is preferred as it is non-invasive, sensitive, accurate and cost-effective.

EXAMPLE 10

Usefulness of $^{13}C$ Glucose Breath Test in Diagnosis of Diabetes

Diabetes mellitus is a group of diseases characterized by high levels of blood glucose resulting from defects in insulin secretion, insulin action, or both. Diabetes can be associated with serious complications and premature death if left undiagnosed and untreated. It has been estimated by the World Health Organization that the number of people suffering from diabetes worldwide will more than double from about 135 million now to 300 million by the year 2025. Of those estimated to have diabetes, it is believed that approximately one third of those are undiagnosed. It is also known that the prevalence of diabetes increases with age. It is estimated that 0.16% of people under the age of 20 have diabetes but this number dramatically increases to 18.4% for people over the age of 65.

There are four types of diabetes; type 1 (insulin dependent) represents 5 to 10% of all diagnosed cases, type 2 (non-insulin-dependent diabetes) represents 90 to 95% of all diagnosed cases, gestational diabetes develops in 2 to 5% of all pregnancies but disappears when a pregnancy is over, and other specific types of diabetes resulting from specific genetic syndromes, surgery, drugs, malnutrition, infections and other illnesses may account for 1 to 2% of all diagnosed cases. A number of different methods exist for determining diabetes. These include postprandial blood glucose, oral glucose tolerance test (OGTT), O'Sullivan glucose tolerance test (gestational test), hemoglobin Alc, islet cell antibodies, glutamic acid decarboxylase (GAD) antibodies, and insulin antibodies. However, diabetes is most readily detected when the carbohydrate metabolic capacity is tested. This is done by stressing the system with a defined glucose load as in the OGTT.

Although the OGTT is a standard test for diabetes, it has been criticized because many of the variables affecting the test results are difficult to control for; the standardized carbohydrate diet, eight to sixteen hour fast, stress, exercise, hormone imbalances, and various drugs can cause test variables. These variables lead to poor reproducibility and limit the diagnostic usefulness of this test. In addition, the OGTT involves the collection of numerous blood specimens making it an invasive procedure.

The development of a $^{13}C$-glucose breath test for the detection of diabetes offers a non-invasive method that is not affected by the above mentioned variables. $^{13}C$ is a non-radioactive isotope that occurs naturally in food and animal tissues. In the past the disadvantage of $^{13}C$ had been the shortage of the gas isotope mass spectrometers used for analysis. With the ready availability of the necessary instrumentation and the $^{13}C$-labeled compounds required, the use of $^{13}C$-labeled compounds in breath tests is more feasible.

Clinical Study

Objective: The primary aim of this pilot study is to evaluate the sensitivity, specificity and reliability of a $^{13}C$-D-glucose breath test in the diagnosis of type 2 and gestational diabetes as compared to the already validated glucose tolerance test that will be considered the standard.

Design: A multi-center, blinded, non-randomized design is utilized. Only the referring physicians have knowledge of the participants' status. Participants undergo a glucose tolerance test. Within two weeks following, participants undergo a $^{13}C$-D-glucose breath test. The findings from both tests are examined for concordance.

STUDY PARTICIPANTS: This investigation is carried out by recruiting 50 individuals each for type 2 and gestational diabetes. For type 2 diabetes, the participants are suspected to be diabetic. For gestational diabetes, the participants are women in their 24th to 28th week of pregnancy who have presented for the standard gestational diabetes mellitus screening test. Any diagnosis of diabetes is based on the results of the glucose tolerance test.

TESTING STRATEGY: Eligible participants, after giving informed consent, undergo the glucose tolerance test and the 13C-D-glucose breath test separated by a minimum of 24 hours and a maximum of two weeks. The glucose tolerance test is performed according to the guidelines of the Canadian Diabetes Association (CMAJ, JAMC Oct. 20, 1998;159(8 suppl):S1–S29). Briefly, for the gestational diabetes screen, the glucose tolerance test consists of the consumption of a 50 g glucose tolerance drink and the collection of a venous blood sample one hour later for glucose determination. For the time between the drink consumption and the blood sampling, the participant remains sedentary and refrains from smoking or eating. Small sips of water may be taken if necessary.

For type 2 diabetes, an overnight fast (10–16 hours) precedes the glucose tolerance test. A fasting glucose blood sample is drawn prior to the consumption of a 75 g glucose tolerance drink. Two hours after the ingestion of the drink, a venous blood sample is collected for glucose determination. For the time between the drink consumption and the blood sampling, the participant remains sedentary and refrains from smoking or eating. Small sips of water may be taken if necessary.

The $^{13}C$-D-glucose breath test is preceded by an overnight fast (minimum eight hours). After fasting, the participants are required to provide a baseline breath sample. The participants then ingest the $^{13}C$-D-glucose drink preparation and will provide breath samples at 1, 1.5, and 2 hours. During the test the participants remain sedentary and are not permitted to smoke or eat. Only small sips of water are permitted during the test.

OVERALL STUDY DESIGN: A total of 50 participants are investigated each for type 2 and gestational diabetes.

Visit One: During the recruitment process, each individual is asked to review a Participant Information Sheet and to talk with the laboratory personnel to ensure that all eligibility requirements are met. The individual is given an opportunity to ask questions and if they meet all the eligibility criteria, they are asked to read and sign an informed Consent Form.

All participants who have met the eligibility criteria and signed a consent form are tested by both the glucose tolerance test (Visit Two) and $^{13}C$-D-glucose breath test (Visit Three) separated by a minimum of 24 hours and a maximum of two weeks.

Visit Two: The glucose tolerance test follows the guidelines set out by the Canadian Diabetes Association (CMAJ, JAMC Oct. 20, 1998;159(8 suppl):S1–S29). Briefly, for the gestational diabetes screen, the participants are asked to consume a commercially available glucose tolerance drink consisting of 50 g of dextrose in 296 mL. One hour following consumption, a venous blood sample is collected into a red-topped vacutainer tube. For type 2 diabetes, participants first complete an overnight fast (10–16 hours) and then provide a fasting blood glucose sample. Participants then ingest a commercially available glucose tolerance drink consisting of 75 g of dextrose in 296 mL followed by the collection of a venous blood sample 2 hours post-consumption.

Visit Three: For the $^{13}$C-D-glucose breath test, participants first complete an overnight fast (minimum of 8 hours). Participants provide a baseline breath sample which is followed by consumption of a $^{13}$C-D-glucose-enriched solution containing 25 mg of $^{13}$C-D-glucose in combination with 15 g of unlabeled USP dextrose in 100 ml of water. Participants then provide breath samples at 1, 1.5, and 2 hours.

Note: Visit One and Visit Two may be combined if it is more convenient and all the testing criteria are met.

NUMBER OF PARTICIPANTS AND TARGET POPULATION: A total of 100 adult participants (18 years of age or older) who are suspected of having type 2 diabetes (n=50) or are being screened for gestational diabetes (n=50) are recruited from those individuals presenting for the oral glucose tolerance test.

INTERIM ANALYSIS: After 25 participants are enrolled for a particular type of diabetes, all parties are unblinded to the participants' status. At this point in the study, the results are evaluated. If the $^{13}$C-D-glucose breath test results do not correlate with the standard, the oral glucose tolerance test, such that greater than 5% of the participants are reported as false negatives or false positives, the study is temporarily halted. If the study is halted, the protocol is amended to reflect an adjustment in the $^{13}$C-D-glucose breath test kit components such that it contains 50 mg of $^{13}$C-D-glucose and 15 g of unlabeled USP dextrose.

EXAMPLE 11

Advantages of the $^{13}$C Glucose Test for the Diagnosis of Diabetes

The disadvantages of the OGTT include uncontrollable factors which cause variability or spurious results and the invasiveness of the test. Other tests known in the art are not specific, are invasive, are variable and are labor intensive. The $^{13}$C glucose breath test of the present invention is sensitive, reliable and specific. The $^{13}$C glucose breath test shows minimal intra-individual variation, excellent analytical precision and breath specimens are stable for at least six weeks at room temperature. The $^{13}$C glucose breath test is preferred over tests known in the art, it is non-invasive, easy to perform, has very good sensitivity and specificity and is cost effective. A preferred use of the breath test of this invention is for the diagnosis of type 2 and gestational diabetes. This invention is also preferred to determine the level of insulin resistance and for monitoring the appropriateness of the therapy of diabetes patients.

Further variations and modification of the present invention will be apparent to those skilled in the art and are intended to be encompassed by the specification and claims appended hereto.

We claim:

1. A diagnostic kit for the determination of baseline glucose metabolism in the absence of an indication of glucose intolerance, diabetes or gestational diabetes in a subject comprising:
   a predetermined quantity of uniformly labeled $^{13}$C-enriched glucose; and
   a breath collection container.

2. A diagnostic kit according to claim 1, said diagnostic kit comprising at least two breath collection containers.

3. A diagnostic kit according to claim 1, said diagnostic kit comprising a first breath collection container for receiving a baseline breath sample taken from the subject prior to ingestion of any the predetermined quantity of the uniformly labeled $^{13}$C-enriched glucose;
   and a second breath collection container for receiving a breath sample after the uniformly labeled $^{13}$C-enriched glucose is ingested.

4. A diagnostic kit according to claim 3, said diagnostic kit further comprising a set of instructions wherein the instructions direct the subject to collect a first breath sample in said first breath collection container, ingest the uniformly labeled $^{13}$C-enriched glucose and collect a second breath sample at a time point that is after ingestion of the uniformly labeled $^{13}$C-enriched glucose, in said second breath collection container.

5. A diagnostic kit according to claim 1, said diagnostic kit further comprising a tube that transfers the breath of the subject into the breath collection container.

6. A diagnostic kit according to claim 1, said diagnostic kit further including analysis means for measuring $^{13}$CO$_2$ metabolized from said uniformly labeled $^{13}$C-enriched glucose, in a breath sample, said analysis means being selected from the group consisting of an isotope ratio mass spectroscope (IRMS), a continuous flow isotope ratio mass spectroscope (CF-IRMS) and a non-dispersive infrared spectroscopy (NDIRS).

7. The diagnostic kit of claim 6 wherein said analysis means is CF-IRMS.

8. The diagnostic kit of claim 6 wherein said analysis means is NDIRS.

9. A diagnostic kit according to claim 1, wherein said predetermined quantity contains 25 mg or less of the uniformly labeled $^{13}$C-enriched glucose.

10. A diagnostic kit according to claim 1, further comprising about 15 g of unlabeled glucose.

11. A diagnostic kit according to claim 1, wherein said predetermined quantity comprises about 25 mg of the uniformly labeled $^{13}$C-enriched glucose.

12. A diagnostic kit according to claim 11, said diagnostic kit comprising a breath collection container for receiving a baseline breath sample taken from the subject prior to ingestion of any of the predetermined quantity of the uniformly labeled $^{13}$C-enriched glucose; and
   at least two breath collection containers for receiving a breath sample at predetermined time points after ingestion of the uniformly labeled $^{13}$C-enriched glucose.

13. A diagnostic kit according to claim 11, said diagnostic kit comprising a first breath collection container for receiving a baseline breath sample taken from the subject prior to ingestion of any of the predetermined quantity of the uniformly labeled $^{13}$C-enriched glucose;
   a second breath collection container for receiving a breath sample at a first time point after ingestion of the uniformly labeled $^{13}$C-enriched glucose and a third breath collection container for receiving a breath sample at a second time point after ingestion of the uniformly labeled $^{13}$C-enriched glucose.

14. A diagnostic kit for the determination of glucose metabolism in a subject comprising a predetermined quantity of uniformly labeled $^3$C-enriched glucose;

a breath collection container for receiving a baseline breath sample taken from the subject prior to ingestion of any of the predetermined quantity of the uniformly labeled $^3$C-enriched glucose; and at least two breath collection containers for receiving a breath sample at predetermined time points after ingestion of the uniformly labeled $^{13}$C-enriched glucose.

15. A diagnostic kit according to claim 14, said diagnostic kit further comprising a set of instructions wherein the instructions direct the subject to collect a first breath sample in the breath collection container, ingest the uniformly labeled $^{13}$C-enriched glucose and collect at least two breath samples at the predetermined time points after ingestion of the uniformly labeled $^{13}$C-enriched glucose in said at least two breath collection containers.

16. A diagnostic kit according to claim 14, said diagnostic kit further comprising a tube that transfers the breath of the subject into the breath collection containers.

17. A diagnostic kit according to claim 14, said diagnostic kit further including analysis means for measuring $^{13}CO_2$ metabolized from said uniformly labeled $^{13}$C-enriched glucose, in a breath sample, said analysis means being selected from the group consisting of an isotope ratio mass spectroscope (IRMS), a continuous flow isotope ratio mass spectroscope (CF-IRMS) and a non-dispersive infrared spectroscopy (NDIRS).

18. The diagnostic kit of claim 17 wherein said analysis means is CF-IRMS.

19. The diagnostic kit of claim 17, wherein said analysis means is NDIRS.

20. A diagnostic kit according to claim 14 wherein said predetermined quantity contains 25 mg or less of the uniformly labeled $^{13}$C-enriched glucose.

21. A diagnostic kit according to claim 14 further comprising about 15 g of unlabeled glucose.

22. A diagnostic kit according to claim 14, wherein said predetermined quantity comprises about 25 mg of the uniformly labeled $^{13}$C-enriched glucose.

23. A diagnostic kit for the determination of glucose metabolism in a subject comprising a predetermined quantity of uniformly labeled $^{13}$C-enriched glucose;

a first breath collection container for receiving a baseline breath sample taken from the subject prior to ingestion of any of the predetermined quantity of the uniformly labeled $^{13}$C-enriched glucose;

a second breath collection container for receiving a breath sample at a first time point after ingestion of the uniformly labeled $^{13}$C-enriched glucose and a third breath collection container for receiving a breath sample at a second time point after ingestion of the uniformly labeled $^{13}$C-enriched glucose.

24. A diagnostic kit according to claim 23 said diagnostic kit further comprising, a set of instructions wherein the instructions direct the subject to collect a first breath sample in said first breath collection container, ingest the uniformly labeled $^{13}$C-enriched glucose, collect a second breath sample at the first time point after ingestion of the uniformly labeled $^{13}$C-enriched glucose in the second breath collection container and collect a third breath sample at the second time point after ingestion of the uniformly labeled $^{13}$C-enriched glucose in the third breath collection container.

25. A diagnostic kit according to claim 23, said diagnostic kit further comprising a tube that transfers the breath of the subject into the breath collection containers.

26. A diagnostic kit according to claim 23, said diagnostic kit further including analysis means for measuring $^{13}CO_2$ metabolized from said uniformly labeled $^{13}$C-enriched glucose, in a breath sample, said analysis means being selected from the group consisting of an isotope ratio mass spectroscope (IRMS), a continuous flow isotope ratio mass spectroscope (CF-IRMS) and a non-dispersive infrared spectroscopy (NDIRS).

27. The diagnostic kit of claim 26, wherein said analysis means is CF-IRMS.

28. The diagnostic kit of claim 26, wherein said analysis means is NDIRS.

29. A diagnostic kit according to claim 23, said predetermined quantity contains 25 mg or less of the uniformly labeled $^{13}$C-enriched glucose.

30. A diagnostic kit according to claim 23, further comprising about 15 g of unlabeled glucose.

31. A diagnostic kit according to claim 23, wherein said predetermined quantity comprises about 25 mg of the uniformly labeled $^{13}$C-enriched glucose.

32. A method for the determination of glucose metabolism in a subject comprising:

a) collecting a first breath sample from said subject in a first breath collection container;

b) administering uniformly labeled $^{13}$C-enriched glucose to said subject;

c) collecting a second breath sample from said subject in a second breath collection container at a time point after administration of said uniformly labeled $^{13}$C-enriched glucose;

d) collecting a third breath sample from said subject in a third breath collection container at a second time point after administration of said uniformly labeled $^{13}$C-enriched glucose;

e) measuring $^{13}CO_2$ in each of said first, second, and third breath samples; and f) comparing the amount of $^{13}CO_2$ in said first, second and third breath samples wherein the difference between said amounts of $^{13}CO_2$ determines the glucose metabolism in the subject.

33. The method of claim 32 wherein steps d) and e) are repeated at least at one additional time point after administration of said $^{13}$C-enriched glucose and said comparison in step f) compares the amount of $^{13}CO_2$ in all breath samples collected.

34. A method of diagnosing a condition in a subject, said condition selected from the group consisting of diabetes, insulin resistance, impaired glucose tolerance, impaired fasting glucose, gestational diabetes and normal glucose metabolism, said method comprising:

a) collecting a first breath sample from said subject in a first breath collection container;

b) measuring a first blood glucose level;

c) administering uniformly labeled $^{13}$C-enriched glucose to said subject;

d) collecting at least a second and third breath sample from said subject in at least a second and third breath collection container, each at a time point after administration of said uniformly labeled $^{13}$C-enriched glucose;

e) measuring $^{13}CO_2$ in each of said first and at least said second and third breath samples and comparing said measurements to obtain delta over baseline (DOB) values;

f) measuring at least a second and third blood glucose level, each at a time point after administration of said uniformly labeled $^{13}$C-enriched glucose;

g) plotting said first and at least said second and third blood glucose levels over time to define a blood glucose test curve;

h) plotting said DOB values over time to define a breath test curve;

i) measuring the areas between said breath test curve and said blood glucose test curve; and k) comparing said areas between said breath test curve and said blood glucose test curve with such areas measured from patients having a condition selected from the group consisting of diabetes, insulin resistance, impaired glucose tolerance, impaired fasting glucose, gestational diabetes and normal glucose metabolism to diagnose said conditions in said subject.

35. The method of claim 34, wherein said condition is diabetes.

36. The method of claim 34, wherein said condition is insulin resistance.

37. The method of claim 34, wherein said condition is impaired glucose tolerance.

38. The method of claim 34, wherein said condition is impaired fasting glucose.

39. The method of claim 34, wherein said condition is gestational diabetes.

40. A diagnostic kit for the diagnosis of a condition in a subject, according to the method of claim 34, the diagnostic kit comprising:

a predetermined quantity of uniformly labeled $^{13}$C-enriched glucose;

a breath collection container; and a blood sampling device.

41. A diagnostic kit according to claim 40, the diagnostic kit comprising a first breath collection container for receiving a baseline breath sample taken from the subject prior to ingestion of any of the predetermined quantity of the uniformly labeled $^{13}$C-enriched glucose; and a second breath collection container for receiving a breath sample after the uniformly labeled $^{13}$C-enriched glucose is ingested.

42. A diagnostic kit for the determination of glucose metabolism in a subject by comparing blood glucose levels with breath levels of $^{13}$C-enriched $CO_2$, said diagnostic kit comprising a predetermined quantity of uniformly labeled $^{13}$C-enriched glucose;

a blood sampling device;

a breath collection container for receiving a baseline breath sample taken from the subject prior to ingestion of any of the predetermined quantity of the uniformly labeled $^{13}$C-enriched glucose; and at least two breath collection containers for receiving a breath sample at predetermined time points after ingestion of the uniformly labeled $^{13}$C-enriched glucose.

* * * * *